(12) United States Patent
Grant et al.

(10) Patent No.: US 11,369,783 B2
(45) Date of Patent: Jun. 28, 2022

(54) SANITIZING ARTICLES FOR LUER ACCESS DEVICES

(71) Applicant: CleanSite Medical, Inc., Solana Beach, CA (US)

(72) Inventors: John Grant, Solana Beach, CA (US); Daniel M. Chambers, Solana Beach, CA (US)

(73) Assignee: CleanSite Medical, Inc., Solana Beach, CA (US)

( * ) Notice: Subject to any disclaimer, the term of this patent is extended or adjusted under 35 U.S.C. 154(b) by 259 days.

(21) Appl. No.: 16/656,552

(22) Filed: Oct. 17, 2019

(65) Prior Publication Data
US 2020/0121910 A1  Apr. 23, 2020

Related U.S. Application Data

(60) Provisional application No. 62/746,556, filed on Oct. 17, 2018.

(51) Int. Cl.
| | | |
|---|---|---|
| *A61L 2/26* | (2006.01) | |
| *A61L 2/18* | (2006.01) | |
| *A61M 39/16* | (2006.01) | |
| *A61M 39/18* | (2006.01) | |
| *B65D 75/28* | (2006.01) | |

(52) U.S. Cl.
CPC ............. *A61M 39/162* (2013.01); *A61L 2/18* (2013.01); *A61L 2/186* (2013.01); *A61L 2/26* (2013.01); *A61M 39/18* (2013.01); *B65D 75/28* (2013.01); *A61L 2202/181* (2013.01); *A61L 2202/24* (2013.01); *A61M 2209/06* (2013.01)

(58) Field of Classification Search
None
See application file for complete search history.

(56) References Cited

U.S. PATENT DOCUMENTS

| | | | | |
|---|---|---|---|---|
| 4,832,942 | A  * | 5/1989 | Grace | A61B 90/80 |
| | | | | 428/305.5 |
| 2004/0234711 | A1 * | 11/2004 | Young | B08B 1/006 |
| | | | | 428/34.1 |
| 2006/0096051 | A1 * | 5/2006 | Akai | A47L 13/20 |
| | | | | 15/104.93 |
| 2008/0038167 | A1 * | 2/2008 | Lynn | A61M 39/20 |
| | | | | 422/294 |
| 2010/0296968 | A1 * | 11/2010 | Cady | A61L 2/186 |
| | | | | 422/28 |
| 2012/0111368 | A1 * | 5/2012 | Rahimy | A61M 39/20 |
| | | | | 134/22.1 |
| 2013/0019421 | A1 * | 1/2013 | Rogers | B08B 1/001 |
| | | | | 15/104.93 |
| 2017/0291054 | A1 * | 10/2017 | Compo | B65B 55/08 |
| 2019/0282795 | A1 * | 9/2019 | Fangrow | A61M 25/0082 |

\* cited by examiner

*Primary Examiner* — Holly Kipouros
(74) *Attorney, Agent, or Firm* — Acuity Law Group, P.C.; Daniel M. Chambers

(57) ABSTRACT

Single-use devices configured to sanitize accessible surfaces of luer access devices (e.g., needleless medical valves) at risk of contamination with infectious agents are described, as are methods for making and using such devices. In particularly preferred embodiments, such devices include a container (e.g., laminated foil pouches or packets) that contain a sanitizing component that includes a substrate with a cleaning port or recess, a cleansing matrix associated with the substrate, and a sanitizing reagent dispersed in the cleansing matrix.

17 Claims, 4 Drawing Sheets

SANITIZING ARTICLES FOR LUER ACCESS DEVICES

RELATED APPLICATION

This application claims the benefit of and priority to U.S. provisional patent application Ser. No. 62/746,556, filed 17 Oct. 2018, which has the same title as and is commonly owned with the instant application, and which is hereby incorporated by reference in its entirety for any and all purposes.

TECHNICAL FIELD

This invention concerns small disposable, single-use devices to sanitize needleless valves on medical fittings, particularly those surfaces of such valves that are or may be at risk of contamination with infectious agents.

BACKGROUND OF THE INVENTION

1. Introduction

The following description includes information that may be useful in understanding the present invention. It is not an admission that any such information is prior art, or relevant, to the presently claimed inventions, or that any publication specifically or implicitly referenced is prior art.

2. Background

Exposure to infectious agents (e.g., pathogenic bacteria, viruses, fungi, etc.) in medical settings is a matter of serious concern. One route of exposure to such agents is the opening made in a patient's skin by the bore of needle, cannula, or other similar device used to provide access to the patient's vasculature. It is known that patients whose skin has been compromised in this way are at increased risk for developing serious blood stream infections. In the United States alone, approximately 300,000 blood stream infections per year result from the installation and use of peripheral intravenous catheters (PIVC), and more than 80,000 blood stream infections are associated with the use central venous catheters (CVC). All told, in the U.S. approximately more than 25,000 patients die annually from healthcare-acquired infections (HAI's) that result from PIVC and CVC use. Costs associated with the care and treatment of patients that develop infections due to PIVC and CVC use exceed several billion U.S. dollars.

In hospital settings today, occupational health and safety regulations designed reduce the risk to health care workers from needle prick and similar injuries have resulted in the deployment of needleless medical valves whenever possible. Currently, more than 1 billion needleless valves are used annually in hospitals throughout the U.S. Needleless valves are used primarily in conjunction with PIVC and CVC devices, in IV sets and extension sets which may contain from as few as one to as many as 3, 4, 5, or more needleless valves. FIG. 1 illustrates an example of a representative medical valve in use today.

The widespread use of needleless valves in acute medicine has contributed to a marked increase in the incidence of hospital-acquired infections (HAIs), particularly blood stream infections (BSIs). To reduce the risk of infection from a contaminated needleless valve, standard practice today requires that a nurse or other health care worker clean the surface of a needleless valve by rubbing it with a sterile alcohol swab or wipe immediately prior to making a connection to the valve, for example, attaching a syringe to the valve to deliver a medication via a PIVC already connected to a patient. Given the magnitude of the mortality and morbidity associated with HAIs and the large number of blood stream infections that result from PIVC and CVC use, a long-recognized yet significant unmet need exists for articles or devices that can be used to reduce or eliminate the risk of initiating an HAI merely by accessing a patient's vasculature through a needleless valve component of a PIVC or CVC inserted into a blood vessel of a patient. The present invention addresses this need through the provision of disposable, single-use devices that can be quickly and easily used to sanitize needleless medical valves.

3. Definitions

Before describing the instant invention in detail, several terms used in the context of the present invention will be defined. In addition to these terms, others are defined elsewhere in the specification, as necessary. Unless otherwise expressly defined herein, terms of art used in this specification will have their art-recognized meanings.

An "aqueous solution" refers to a water-based solution capable of dissolving or dispersing one or more other substances, or solutes (i.e., the substance(s) dissolved in the solvent). A "solution" is a homogeneous mixture of at least one substance in a liquid. In the context of this invention, "aqueous solvents" can also include other liquids, including organic liquids, such as alcohols (e.g., isopropyl alcohol) and/or oils.

An "infectious agent" refers to any organism capable of infecting another organism. Such agents include many bacteria, viruses, and fungi.

A "patentable" composition, process, machine, or article of manufacture according to the invention means that the subject matter at issue satisfies all statutory requirements for patentability at the time the analysis is performed. For example, with regard to novelty, non-obviousness, or the like, if later investigation reveals that one or more claims encompass one or more embodiments that would negate novelty, non-obviousness, etc., the claim(s), being limited by definition to "patentable" embodiments, specifically excludes the unpatentable embodiment(s). Also, the claims appended hereto are to be interpreted both to provide the broadest reasonable scope, as well as to preserve their validity. Furthermore, if one or more of the statutory requirements for patentability are amended or if the standards change for assessing whether a particular statutory requirement for patentability is satisfied from the time this application is filed or issues as a patent to a time the validity of one or more of the appended claims is questioned, the claims are to be interpreted in a way that (1) preserves their validity and (2) provides the broadest reasonable interpretation under the circumstances.

A "plurality" means more than one.

"Sanitizing association" and the like refer to bringing two articles together such that one can be used to sanitize, or clean, the other.

A "sanitizing operation" refers to moving, for example, a needless medical valve in relation to a sanitizing device of the invention, preferably by rotating the valve in relation to the sanitizing device. This can be accomplished, for example, by a user grasping a needleless medical valve in one hand, sanitizingly associating it with a device according to the invention being held in the other hand, and rotating the valve and sanitizing device in relation to each other for a desired period (e.g., about 5-30 seconds). If desired, the user may also vertically displace the valve and sanitizing device in relation to each other before, during, and/or after device/valve rotation.

"Single-use" (or "single purpose") refers to an article or device suitable for one use or purpose only, as distinguished from "dual" or "multiple" use or purpose devices. Thus, in the context of the invention, a "single-use" sanitizing article or device is one that is useful for sanitizing, for example, a luer access device such as needleless medical valve.

In a "suspension" solid particles are dispersed in a liquid. The term "colloidal" refers to a state of subdivision, which, in the context of solutions, means that molecules or particles dispersed in the liquid have at least in one direction a dimension roughly between 1 nm and 1 μm. It is not necessary for all three dimensions to be in the colloidal range. A "colloidal dispersion" is a system in which particles of colloidal size of any nature (e.g. solid, liquid or gas) are dispersed in a continuous phase of a different composition (or state). In an "emulsion" liquid droplets and/or liquid crystals are dispersed in another liquid. An emulsion may be denoted by the symbol "O/W" if the continuous phase (i.e., is an aqueous solution) and by "W/O" if the continuous phase is an organic liquid.

DESCRIPTION OF THE INVENTION

It is an object of this invention to provide patentable single-use sanitizing devices or articles that can be used to effectively and efficiently sanitize, and preferably sterilize, exposed surfaces of luer access devices such as needleless medical valves, particularly the accessible surface (which frequently includes one or more threads or threaded portions, tabs, or the like) of their valve stems, which surfaces that may become contaminated with infectious agents. In the context of the invention, "sanitize" encompasses cleaning, disinfecting, and/or sterilizing.

Thus, one aspect of the invention concerns patentable single-use sanitizing articles configured to sanitize needleless valves of luer access devices. Sanitizing devices, or articles, according to the invention are sealed, sterilized single-use devices that, once unsealed and used to sanitize a luer access device such as a needleless medical valve, can be disposed of. In this aspect, the sanitizing devices of the invention typically comprise a multi-part sanitizing component associated with a sealed, single use container or pouch that can be easily opened to expose the sanitizing component. In preferred embodiments of this aspect, and unlike conventional IPA wipes, the multi-part sanitizing component of an article is not removed from its container prior to use; in other embodiments, the multi-part sanitizing component may be removed from the pouch before use.

In those embodiments where the sanitizing component is not removed from the container prior to use, the sanitizing component remains inside or otherwise associated with at least a portion of the container, in some embodiments by being fixedly associated with at least part of an inner surface of a portion or region of one or more layers of the container (e.g., via adhesive, a mechanical association, or any other suitable way of fixedly associating the sanitizing component to at least a portion of an inner surface of the container). In these embodiments, in order to expose the sanitizing component the container includes an access port through which the sanitizing component can be accessed inside the container. To maintain sterility and retain the sanitizing component inside the container, the device typically includes a partially or completely peelable or removable cover adhered (for example, via a suitable adhesive), attached (e.g., via heat sealing, ultrasonic welding, or the like), or otherwise sealing associated to or with the outer surface of a portion or region of the container near or adjacent to the access port, which cover covers the access port and seals the container until the cover is removed. After removal, a user can insert a luer access device through the access port such that the valve region of the luer access device, preferably, for example, including its threaded valve portion, can contact the sanitizing component.

In other embodiments, when the container is opened, for example, by being torn open or peeled apart just prior to use by a health care worker, the multi-part sanitizing component can be removed from the container prior to use.

In the devices of the invention, a multi-part sanitizing component is configured to accommodate the three dimensional structure of the valve portion (or region) of a luer access device such as a needleless medical valve so as to allow those surfaces of the valve (including the valve surface and its adjacent regions, and preferably some or all of the threaded portion of the valve) that are likely to be contaminated and which may form part of the fluid communication pathway between an external fluid source and a patient's blood stream to be easily sanitized immediately prior to attachment of a fluid reservoir to the luer access device (e.g., needleless medical valve).

In this aspect of the invention, a multi-part sanitizing component comprises a substrate, a cleansing matrix associated with the substrate, and a sanitizing reagent dispersed in the matrix. In many preferred embodiments, the sanitizing reagent is dispersed in the cleansing matrix at the time the device is manufactured and before the pouch is sealed. Of course, the invention also includes embodiments where the sanitizing reagent is released for dispersion into the cleansing matrix post-manufacture or post-sealing, but prior to the time the device is brought into contact with the luer access device to be sanitized. In such embodiments, the sanitizing reagent is preferably stored in a reservoir or other reagent container that is ruptured (e.g., by an applied external force) to release the sanitizing reagent for dispersion in the cleansing matrix.

The substrate of a sanitizing device of the invention is typically a flexible, rigid, or semi-rigid element used to support the cleansing matrix when the device is being used to sanitize the valve region of a luer access device. The substrate includes an cleaning port (i.e., an opening or hole) or recess sized to accommodate the valve region of a luer access device and the associated region of the cleansing matrix as a luer access device's valve region and associated cleansing matrix region are pushed into the cleaning port or recess so as to facilitate high friction contact between the device's valve region and associated cleansing matrix region, as will occur when a user sanitizingly associates the valve region of a luer access device with the cleansing matrix region prior to and during a sanitizing operation. Because luer access devices such as needleless medical valves often have exposed surfaces with complex external shapes, the article's sanitizing component should be sufficiently compliant and resilient so as to readily conform to the surface features of the luer access device to be sanitized.

To facilitate conforming the sanitizing component to the surface(s) of the luer access device to be sanitized, the substrate includes a cleaning port or recess sized to allow insertion therein of the portion of the luer access device to be cleansed, in addition to that portion of the cleansing matrix associated with the luer access device, when a user brings the luer access device to be cleansed into sanitizing association with the cleansing matrix. Preferably, while the cleaning port is sized to accommodate the valve region of a luer access device (e.g., a needleless medical valve or connector) and the associated region of the cleansing matrix, it is not so large as to allow the entire luer access device to be inserted through the opening. As will be appreciated, luer access device such as needleless connectors have a collar or region with a larger diameter adjacent to the threaded portion to be cleaned. While the cleaning port is sized to accept the needleless connector's threaded valve region and the region of the cleansing matrix brought into association therewith, the cleaning port's diameter preferably is not large enough to accommodate adjacent regions of the luer access device (e.g., needleless connector), making it easier for a healthcare worker to use the device of the invention to sanitize the, for example, needleless connector.

Generally, the cleaning recess or port has a diameter larger than the outer diameter of the portion of the luer access device (e.g., the valve portion) to be cleansed. Preferably, the diameter of the recess or port is 1.05-2 times that of the outer diameter of the portion of the luer access device (e.g., the valve portion) to be cleansed. As will be appreciated, the diameter of the cleaning port or recess of a particular sanitizing device of the invention will depend on several factors, including the type of material(s) constituting the cleansing matrix, the thickness of the matrix, the sanitizing reagent dispersed therein, etc. Additionally, in those embodiments where the substrate includes a recess to facilitate engagement of the cleansing matrix of the sanitizing component with that portion of a luer access device to be cleansed in a sanitizing operation, the depth of the recess preferably is sufficient to allow that portion of a luer access device to be cleansed to be engaged by (i.e., sanitizingly associated with) the cleansing matrix. The recess (or well) can be partially or fully closed at the bottom, and if desired it may also contain additional friction-providing structures (e.g., bumps, ridges, etc.) or materials (e.g., compressible foam) disposed therein. As with other embodiments of the invention, the relative movement between the sanitizing article and luer access device, such as provided by a user rotating and/or pushing and/or pulling one of the sanitizing article and/or luer access device in relation to the other produces friction sufficient to "scrub" the surface(s) of the luer access device contacted by the cleansing matrix to disrupt, and preferably remove therefrom, some or all of the contaminating microorganisms (which may or may not be part of a biofilm), which microorganisms may pose a threat of infection should at least some of them be introduced into a patient's bloodstream.

In some embodiments, the cleaning port or recess includes one or more engaging features to promote sanitizing association between a sanitizing article of the invention and that portion of a luer access device to be cleansed. Such engaging features include threads or one or more partially or fully female-threaded regions complementary to the male-threaded valve portion of a luer access device. In such embodiments the females threads of the sanitizing article are sized to accommodate male threads from the luer access device and an intervening layer of material comprised of portions of the cleansing matrix adjacent to the male threads during a sanitizing operation. In other embodiments, the engaging feature(s) is(are) a crushable tab (or series of such tabs), resilient elements that project downward from the bottom of the substrate that are formed to provide substantially equal pressure (or force) to the cleansing matrix along that portion of its length that sanitizingly associates with that portion of a luer access device inserted through (or into) the cleansing port (recess) (well)).

The cleansing matrix of a sanitizing component includes a sanitizing region configured to engage one or more accessible surfaces of a valve region of a luer access device so as to expose the accessible surface(s), and any infectious agents residing thereon, to the sanitizing reagent. Also, because valve surfaces may be contaminated with microorganisms that form a biofilm (i.e., a matrix of microorganisms and extracellular material attached to a surface, which enables the microorganisms, typically bacteria and/or fungi, to adhere to a surface and carry out certain biochemical processes), the cleansing matrix also preferably has sufficient mechanical integrity to allow its use to disrupt the biofilm, such as can occur by rotating, twisting, or otherwise moving the sanitizing component in relation to the needleless medical when the sanitizing device is brought into contact with the valve.

In some embodiments, the cleansing matrix comprises a single layer of substantially uniform thickness, whereas in others, it comprises a single layer of varying thickness that may have contours or features designed to enhance sanitizing contact with the surface(s) to be cleaned. Alternatively, the cleansing matrix can be made from a plurality of layers, each of which may be of substantially uniform or varying thickness(es), and which together are integrated to form a substrate of desired thickness(es) and surface contour(s). In some embodiments, the layers of the matrix are substantially uniform thickness and are formed into layers by folding a larger piece of matrix material upon one or more fold lines. In devices that have a multi-layered matrix, the material used to form each layer may be of the same or different material, may be of the same or different dimensions (length, width and/or thickness), and may or may not contain a sanitizing reagent. When two or more layers each contain a sanitizing reagent, the reagent may the same or different, although preferably they are compatible such that one reagent does not appreciably degrade the sanitizing capacity of the other. Additionally, in some embodiments of multi-layer devices, one ore more of the layers may be physically separated from the other layer(s) by an impermeable, semi-permeable, or permeable barrier, one, some, or all of which other layers may also contains materials such as heat-activated dyes or coloring agents.

In preferred embodiments, the cleansing matrix used to form the sanitizing element is any suitable absorbent material that is pliable, fibrous, and/or porous, or combination of materials that can be wetted and/or impregnated with a sanitizing reagent. Such materials include those that are synthetic or naturally occurring, and they may be of homogeneous or heterogeneous composition, and include materials where natural and synthetic materials are blended. Preferred synthetic materials include woven or non-woven fibers, foams, and gel compositions. Preferred natural materials include those derived from fibrous materials such as cotton and silk, which materials can be spun and woven, as well as materials such as natural sponges. With respect to synthetic fibrous materials, those having directly oriented fibers are particularly preferred. In embodiments wherein the sanitizing component is comprised of two or more layers, each layer can be formed from a material that is the same as or different from the material used to form the other layer(s), and each layer may contain the same, different, or even no, sanitizing reagent (although at least one layer will have a sanitizing reagent dispersed therein prior to engaging the surface of the needleless valve to be sanitized). Also, even when materials for different layers are formed from the same material, they may be configured differently. For example, in one particularly preferred embodiment that employs a sanitizing component having two layers, the material for the upper and lower layers is formed from a natural material such as woven or spun cotton. In other embodiments that employ a matrix having two or more layers, the material(s) for the uppermost layer(s) is(are)(i.e., the layer(s) designed to contact the valve region of the luer access device) formed from an absorbent synthetic material (e.g., an absorbent synthetic material having directionally oriented fibers or a synthetic foam pad) that also has mild abrasive characteristics, while the material(s) for the lower layer(s) is(are) an absorbent pad formed from a natural material such as woven or spun cotton. When cleansing matrix components are made from two or more layers of different materials, preferably the layers are adhered or otherwise associated at an interface using a suitable adhesive or other joining material to allow the layers to remain associated during use.

In embodiments where the cleansing matrix includes an upper layer comprised of a material having abrasive characteristics in order to achieve improved sanitizing of the potentially contaminated exposed surface(s) of a luer access device (e.g., a needleless medical valve), such abrasive layer or material may or may not comprise a sanitizing reagent dispersed therein during manufacture; however, any such layer allows sanitizing reagents disposed in other layers of the sanitizing component to reach the valve surface(s) to be sanitized during a sanitizing operation.

The sanitizing component of sanitizing devices of the invention also includes one or more sanitizing reagents dispersed therein prior to opening the device. Sanitizing reagents comprise at least one active ingredient capable of sanitizing a surface of a needleless medical valve. Any active ingredient, or combination of active ingredients, that can be used effectively to rapidly sanitize a luer access device (e.g., a needleless medical valve) can be adapted for use in practicing the invention, and are generally classified as antibacterial and antifungal agents, antiseptic or antimicrobial agents, wide spectrum disinfectants, and/or parasiticides, as well as combinations of such reagents. Particularly preferred are biocompatible active ingredients and sanitizing reagents, as the devices of the invention are intended for human and/or veterinary use, including alcohols, antibiotics, oxidizing agents, and metal salts. Sanitizing reagents are preferably in liquid form, with the liquid wetting the substrate. In other embodiments, the substrate is dry and contains a sanitizing reagent dispersed therein. Preferably a sanitizing reagent does not appreciably cross-react with materials from which luer access devices are constructed, and is compatible with the materials used to form the substrate, cleansing matrix, and container in which the sanitizing component container of a sanitizing article according to the invention.

In another aspect, the patentable single-use sanitizing articles comprise a container formed to provide a sealed internal cavity and which comprises an access port sealingly covered by a cover removably adhered or attached to an exterior portion of the container surrounding the access port that, when removed, allows access to the internal cavity of the container, and disposed in the internal cavity of the container, a sanitizing component that includes a cleansing matrix associated with the substrate and covering cleaning port or recess; a sanitizing reagent dispersed in the matrix; and, optionally a substrate comprising a cleaning port or recess. As with other aspects of the invention, the devices of this aspect are preferably manufactured to be sterile (i.e., by sterilizing the devices during manufacture, after individual device assembly and packaging; any sterilization process compatible with the various components of the article and its packaging can be used). As will be appreciated, in this aspect the articles of the invention do not require a substrate; however, the sanitizing component, be it comprised of a sanitizing matrix in the absence of a substrate or be it comprised of a sanitizing matrix and a substrate, is designed to remain in the container during use. As will be appreciated, in other regards the articles of this aspect are comparable to those of the other aspects of the invention.

In the articles of the invention, the sanitizing component is disposed in a sealed, easily opened container having at least two layers formed from any suitable material, or combination of materials. Representative examples of such containers include pouches and packets. Here, a "pouch" or "packet" refers to a structure made to contain at least two layers, an upper (or first) layer and a lower (or second) layer, joined together (i.e., "sealed") about their peripheries to form at least one internal cavity adapted to a contain a sanitizing element. The layers may be formed from separate pieces of the same or different material(s); alternatively, they may be formed from the same piece of material such that they can be joined to produce the desired container configuration. For example, a piece of material having the dimensions: length=2X and width=X can be folded about an axis such that upon folding, each of the upper and lower layers have length and width dimensions equal to X. Accordingly, suitable containers can be formed from combinations of separate and/or folded pieces of any suitable material, or combination of materials. Particularly preferred multi-layered containers are laminated foil pouches or packets formed to have an internal cavity in which the sanitizing element is disposed.

Depending upon the particular container configuration and material(s) used, in order to use the device to sterilize a luer access device, e.g., a needleless medical valve, the container must be opened to expose the sanitizing component in those embodiments in which the sanitizing component is not removed from the container prior to sanitizing the luer access device. In general, a user (e.g., a health care worker) can open the container in any suitable way, such as by tearing or cutting it open to remove the sanitizing component or, in embodiments where the sanitizing component is designed to remain in the container during a sanitizing operation, such as peeling off a removable cover or tab covering an access port in the container and adhered to a portion of the outer surface of the container, which removal exposes the sanitizing component housed inside the container.

In general, the sealed single-use sanitizing articles of the invention are sterile, labeled, and packaged in bulk and provided to health care providers in bulk.

Other aspects of the invention relate to patentable methods of making and using the sanitizing articles of the invention, for example, to produce at least about a 10-fold reduction in microorganism contamination on the accessible surface of a valve portion of a luer access device, optionally more than a 100-fold, a $10^3$-fold, a $10^4$-fold, a $10^5$-fold, a $10^6$-fold, or $10^7$-fold reduction in microorganism contamination. Other patentable methods of the invention concern reducing a patient's risk of contracting an HAI, particularly a catheter-related blood stream infection. Still other aspects concern hand-held machines that use sanitizing articles of the invention to sanitize needleless medical valves.

Other features and advantages of the invention will be apparent from the following drawings, detailed description, and appended claims.

DESCRIPTION OF REPRESENTATIVE EMBODIMENTS

Figure 2:
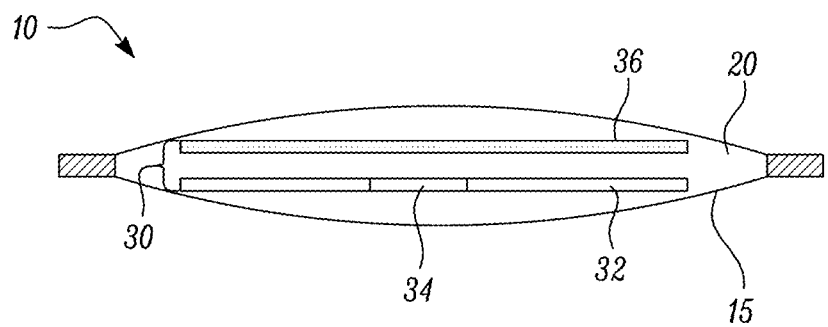
FIGS. 2-10 show several drawings of different representative embodiments of sanitizing articles according to the invention and some of the components thereof.
Figure 3:
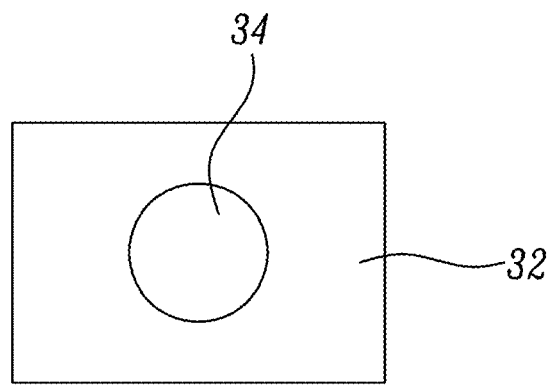

FIGS. 2-10 depict several representative embodiments of sanitizing articles according to the invention. FIG. 2 shows a cross-section of a sanitizing article (10) having a sealed container 15 that forms an internal cavity (20) in which a multi-part sanitizing component (30) is disposed. Preferably, such an article is provided to end users in sterile form, although sterilization is not essential in all embodiments. The sanitizing component (30) shown has two parts, a cleansing matrix (36) and a substrate (32). The substrate (32) includes a cleaning port or recess (34), and is in a top (or bottom) view in FIG. 3. The cleansing matrix (36) includes a sanitizing reagent (shown as particles) dispersed therein. As will be appreciated, in the embodiment shown in this Figure, the sanitizing article's container does not contain an access port or a removable cover (see instead FIG. 8, described below); instead, the article (10) is designed to be opened (for example, by peeling, tearing, or otherwise opening the container (15)) and the sanitizing component (30) removed therefrom prior to use to sanitize a luer access device (not shown).

Figure 4A:
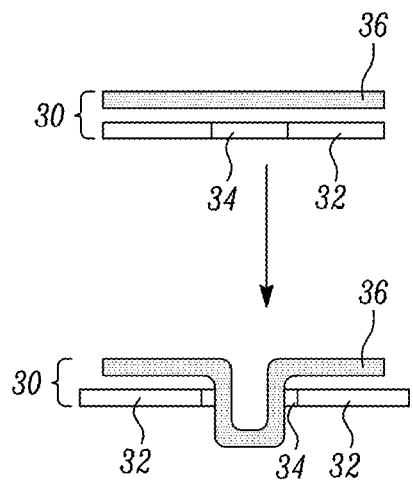
Figure 4B:
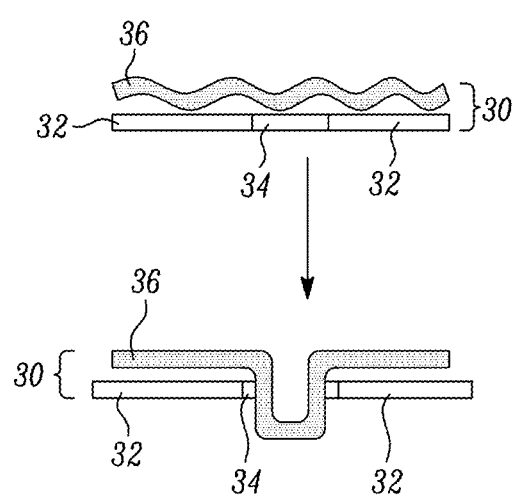

FIG. 4 has 2 panels, panel FIG. 4A and panel FIG. 4B. Each panel shows a different embodiment of representative associations between the cleansing matrix (36) and substrate (32) of two different representative sanitizing component (30) structures. These sanitizing component (30) structures can be employed in embodiments of the invention wherein they remain inside the sanitizing article (10) and are thus accessed through an access port (16) in the container (15) or after they have been removed from the container (15).

In panel FIG. 4A, the upper drawing shows a substrate (32) underneath a substantially flat cleansing matrix (36) impregnated with a sanitizing reagent. To use the sanitizing component (30) (for example, after removing it from a container), a user would push the portion of the luer access device to be sanitized into the cleansing matrix (36) so as to force the luer access device and cleansing matrix into the cleaning port (34) so as to bring the luer access device and cleansing matrix into sanitizing association, as shown in the lower drawing of panel 4A.

Similarly, in panel FIG. 4B, the upper drawing shows a substrate (32) underneath a bunched cleansing matrix (36) impregnated with a sanitizing reagent. Here, the bunched cleansing matrix (36) is larger than that shown in panel FIG. 4A so as to ensure that as the matrix is pushed into the cleaning port (34), sufficient material remains so as to prevent some or all of the cleansing matrix from being completely pushed through the cleaning port (34), which could reduce the association between the matrix and luer access device in the region being cleaned, thus possibly limiting the efficacy of the device. To use the sanitizing component (30) (for example, after removing it from a container), a user would push the portion of the luer access device to be sanitized into the cleansing matrix (36) so as to force the luer access device and cleansing matrix into the cleaning port (34) so as to bring the luer access device and cleansing matrix into sanitizing association, as shown in the lower drawing of panel FIG. 4B. During this process, a user will preferably rotate the luer access device and cleansing matrix in relation to each other while it is in sanitizing association with the cleansing matrix so as to optimize the mechanical friction between the luer access device and cleansing matrix. As will be appreciated, such pushing and rotating provides a scrubbing action to sanitize a portion of the luer access device. Again, such a sanitizing component (30) structure can be employed in embodiments of the invention wherein it remains inside a sanitizing article (10) and is thus accessed through an access port (16) in the container (15) or after it has been removed from the container (15)

Figure 5:
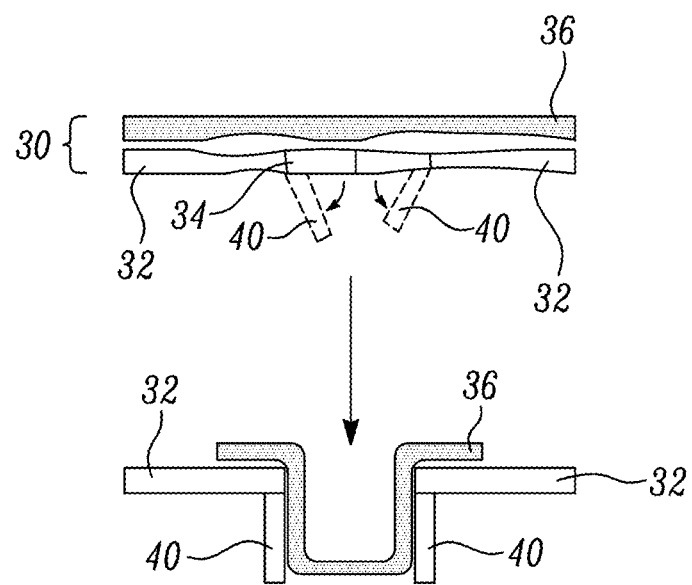

FIG. 5 shows two drawings of a representative embodiment of a sanitizing component wherein the substrate includes engaging structures (40) to further facilitate sanitizing association between the substrate (32) and cleansing matrix (36). As shown in the embodiment depicted in FIG. 5, the engaging structures (40) begin in the same plane as the substrate and are defined by the perimeter of the cleaning port (34). As a luer access device is pushed into the cleansing matrix (36) and into the cleaning port (34), the engaging structures (40) are pushed downward. Here, they may be, for example, pie slice-shaped pieces of material in a region of the substrate that has been processed to produce such features, for example, by scoring the surfaces of the substrate to provide for such pieces when another item, for example, a needlefree connector and associated portion of a cleansing matrix, are pushed into the substrate with sufficient force so as to cause the engaging structures (40) to be pushed downward and apart from each other. Those in the art will also appreciate that the invention envisions the use of any suitable engaging structure, or set of structures, to provide the functionality of forming a sanitizing association between region of a luer access device and the cleansing matrix. This also includes adding another article, e.g., an engaging element insert, to the substrate in the region of the cleaning port. In many embodiments, it is desirable that the engaging elements (40) have some degree of resilience so as to facilitate formation and maintenance of a sanitizing association, including friction, between the luer access device and cleansing reagent. As is the case with other embodiments, such a sanitizing component (30) structure can be employed in embodiments of the invention wherein it remains inside a sanitizing article (10) and is thus accessed through an access port (16) in the container (15) or after it has been removed from the container (15)

Figure 6:
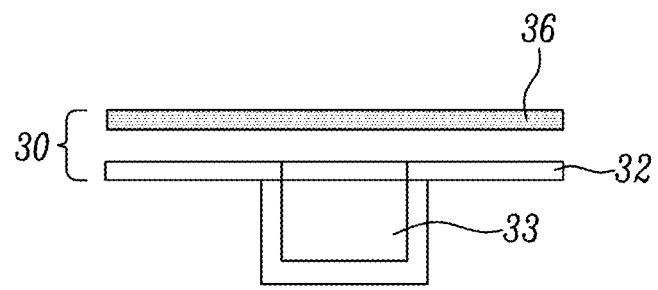
Figure 6:
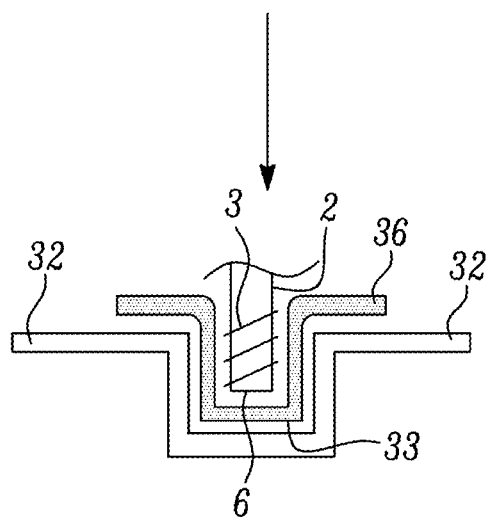

FIG. 6 contains two drawings, an upper drawing and a lower drawing, each showing a cross-section of a sanitizing component (30) in which the substrate includes a recess that forms a well (33). The upper drawing shows a cross-section of a sanitizing component (30) prior to insertion of a luer access device such as a needleless connector. The lower drawing shows the same sanitizing component (30) after to insertion of a luer access device into the cleansing matrix (36) and into the well (33). Again, such a sanitizing component (30) structure can be employed in embodiments of the invention wherein it remains inside a sanitizing article (10) and is thus accessed through an access port (16) in the container (15) or after it has been removed from the container (15).

Figure 7A:
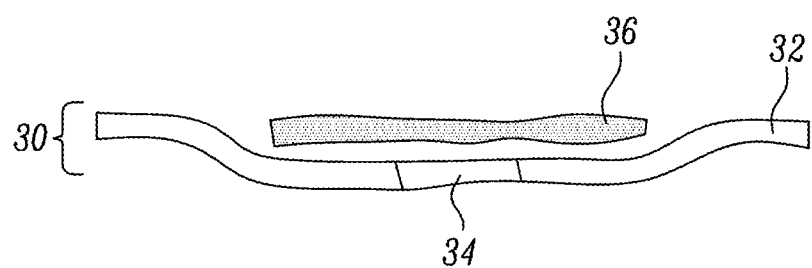
Figure 7B:
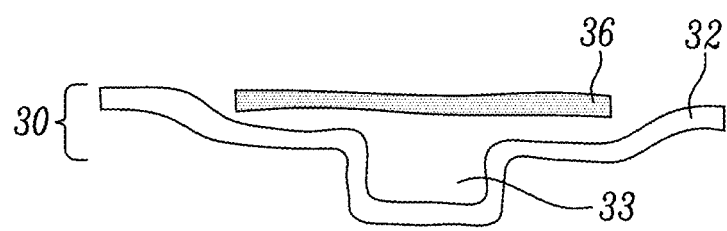

FIG. 7 also contains two drawings, an upper drawing, FIG. 7A and a lower drawing, FIG. 7B, each of which shows a cross-section of yet another sanitizing component (30) embodiment in which the substrate (32) includes a depression adapted to receive the cleansing matrix (36) that contains a sanitizing reagent. In the lower drawing, FIG. 7B, the substrate (32) further includes a cleansing recess that forms a well (33) in a portion of the substrate that contains the depression adapted to receive the cleansing matrix (36). As is the case for many embodiments, sanitizing component (30) structures such as shown in FIG. 7 can be used in embodiments wherein it remains inside a sanitizing article (10) and is thus accessed through an access port (16) in the container (15) or after it has been removed from the container (15).

Figure 8:
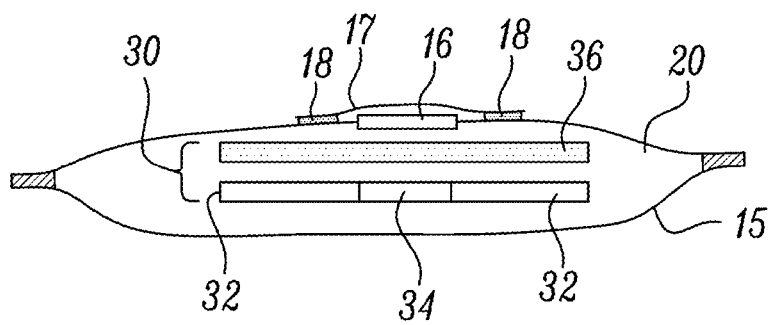

FIG. 8 is an illustration showing a representative embodiment of a sanitizing article (10) wherein the sanitizing component (30) is retained in the internal cavity (20) of the container (15) and is accessed via a access port (16) or opening in the upper portion of the container (15) after removal of a removable cover (17) adhered or otherwise attached so as to seal the container until the cover (17) is removed, for example, by peeling. The cover (17) can be attached to an outer surface of the container (15) using any approach suitable for the particular materials, etc. Such attachment can be, for example, through the use of a suitable adhesive (18), by heating sealing, ultrasonic welding, or the like. The sanitizing component (30) is typically positioned in the internal cavity (20) of the container (15) such that the cleansing matrix is disposed between the substrate (32) and access port (16). When the cover (17) is removed (e.g., peeled off) from the sanitizing article (10), the access port (16) is exposed. A user wishing to sanitize a needleless connector, for example, can then insert the connector through the access port (16). This allows the valve portion (2) of the connector to contact the cleansing matrix (36) and, as the user further pushes the connector into the sanitizing article (10), the cleansing matrix (36) and valve portion (2) are inserted into the cleaning port (34) (or recess; see, e.g., FIG. 6) in sanitizing association. Rotation of the sanitizing article (10) in relation to the connector (1), by movement of one, the other, or both of them, for example, for 1-30 or more seconds, allows the connector (or other luer access device) to be sanitized. Such sanitizing is preferably performed immediately before a fluid connection is made to the luer access device. Compliance with such "scrub the hub" procedures helps to reduce the risk that a patient into whom fluid was administered via such luer access device will contract a blood stream infection due to microbial contamination. Those in the art will appreciate that other multi-part sanitizing component configurations, for example, those shown in FIGS. 4, 5, 6, 7, and 9, can alternatively be used.

Figure 9:
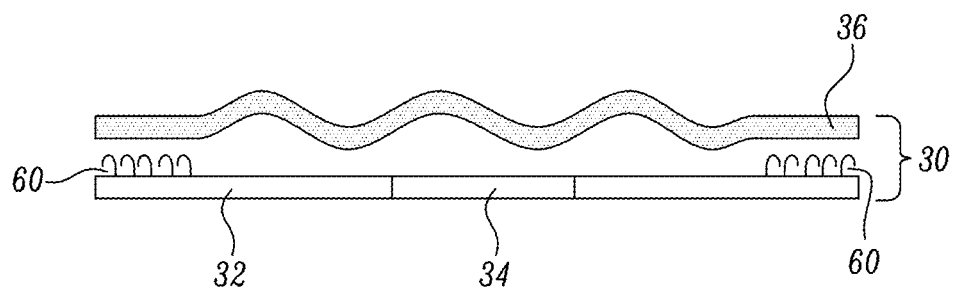

FIG. 9 is an illustration of another representative embodiment of a multi-part sanitizing component (30) useful in practicing the invention. In this and related embodiments, the surface of the substrate (32) that faces the cleansing matrix (36) includes one or more retention features or elements (60) that engage one or more areas of the cleansing matrix (36) to help it. Such embodiments preferably utilize cleansing matrices (36) that include sufficient extra material to allow a portion of it to extend into and through the cleaning port when pushed into it by a luer access device.

Figure 1:
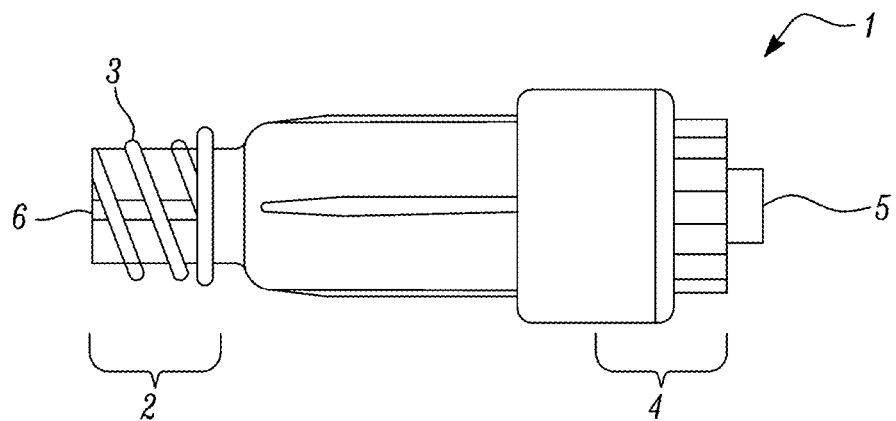
FIG. 1 is a drawing of a representative needleless connector (1), a type of luer access device suited for cleansing by the devices and methods of the invention. The needleless connector shown is a valve or port that provides a flow path (6 to 5) through the valve's proximal end (2) to its distal end (4). The proximal end (2) has luer threads (3) that allow it to be connected to a complementary female luer fitting. The distal end (4) includes a female luer fitting adapted to engage the threaded male portion of another device.
Figure 10:
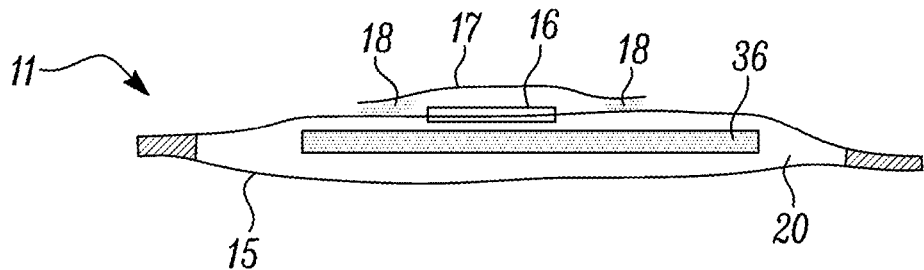

FIG. 10 shows a representative embodiment of the invention wherein the sanitizing component lacks a substrate. Instead, the sanitizing article (11) contains a sanitizing matrix (36) housed in a container (15) that includes an access port (16) and cover (17) therefor adhered or otherwise attached to the container's (15) upper surface. In use, the lower portion of the container, beneath the sanitizing matrix (36), can be used as the substrate. For example, a user could grip the sanitizing article (11) between the fingers of one hand and remove and discard the cover (17) with her/his other hand. S/he could then grasp a luer access device, for example, a needleless connector (see, e.g., FIG. 1) with her/his free hand and insert its threaded valve portion into the article's internal cavity (20) so as to bring it into contact with the sanitizing matrix (36). The user's gripping action of the container can form a well into which the sanitizing matrix (36) and luer access device can be brought into sanitizing association such that the luer access device can then be sanitized.

Again, such a sanitizing component (30) structure can be employed in embodiments of the invention wherein it remains inside a sanitizing article (10) and is thus accessed through an access port (16) in the container (15) or after it has been removed from the container (15).

All of the compositions, articles, and methods described and claimed herein can be made and executed without undue experimentation in light of the present disclosure. While the, articles and methods of this invention have been described in terms of preferred embodiments, it will be apparent to those of skill in the art that variations may be applied to the articles, methods, and compositions without departing from the spirit and scope of the invention. All such variations and equivalents apparent to those skilled in the art, whether now existing or later developed, are deemed to be within the spirit and scope of the invention as defined by the appended claims.

All patents, patent applications, and publications mentioned in the specification are indicative of the levels of those of ordinary skill in the art to which the invention pertains. All patents, patent applications, and publications are herein incorporated by reference in their entirety for all purposes and to the same extent as if each individual publication was specifically and individually indicated to be incorporated by reference in its entirety for any and all purposes.

The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A patentable single-use sanitizing article configured to sanitize a needleless medical valve, or portion thereof, the article comprising:
   a. a laminated foil container formed to provide a sealed internal cavity, wherein the laminated foil container comprises an access port sealingly covered by a cover removably adhered or attached to an exterior portion of the laminated foil container surrounding the access port such that when the cover is removed the access port allows access to the internal cavity of the laminated foil container; and
   b. disposed in the internal cavity and accessible via the access port, a sanitizing component comprising:
      (i) a cleansing matrix;
      (ii) a sanitizing reagent dispersed in the cleansing matrix; and
      (iii) a substrate associated with the cleansing matrix, wherein the substrate comprises a cleaning port or recess that is alignable with the access port of the laminated foil container and wherein at least a portion of the cleansing matrix is disposed between the container's access port and the substrate's cleaning port or recess.

2. An article according to claim 1, wherein the cleansing matrix comprises an absorbent material selected from the group consisting of a naturally occurring material and a synthetic material, wherein when the cleansing matrix is a naturally occurring material, the naturally occurring material is optionally a natural sponge, and wherein when the cleansing matrix is a synthetic material, the synthetic material is optionally selected from the group consisting of a fibrous composition, a foam, and a gel.

3. An article according to claim 1, wherein the sanitizing reagent is a liquid formulation, optionally an aqueous solution, optionally a solution comprising an alcohol and water, optionally isopropyl alcohol and water, optionally 70% isopropyl alcohol and water.

4. An article according to claim 1, wherein the sanitizing reagent comprises one or more sanitizing compounds selected from the group consisting of an alcohol, chlorhexidine, hydrogen peroxide, iodine, silver ions, and a combination of any two or more of the foregoing.

5. An article according to claim 1, wherein the laminated foil container comprises an upper portion and a lower portion, which upper and lower portions are sealed to each other about their peripheries.

6. An article according to claim 1, wherein an outer surface of the laminated foil container is labeled.

7. An article according to claim 1 wherein the substrate's cleaning port or recess is sized to accommodate a portion of the cleansing matrix and a valve portion of a needleless medical valve when the valve portion of the needleless medical valve is in sanitizing association with the cleansing matrix during a sanitizing operation.

8. An article according to claim 1 that is sterile.

9. A package comprising a plurality of articles according to claim 1.

10. A patentable single-use sanitizing article configured to sanitize a luer access device, optionally a needleless medical valve, or portion thereof, the article comprising:
   a. a laminated foil container formed to provide a sealed internal cavity, wherein the laminated foil container comprises an access port sealingly covered by a cover removably adhered or attached to an exterior portion of the laminated foil container surrounding the access port such that when the cover is removed the access port allows access to the internal cavity of the laminated foil container; and
   b. disposed in the internal cavity and accessible via the access port, a sanitizing component comprising:
      (i) a cleansing matrix;
      (ii) a sanitizing reagent dispersed in the cleansing matrix; and
      (iii) a substrate associated with the cleansing matrix, wherein the substrate comprises a cleaning port or recess that is alignable with the access port of the laminated foil container and wherein at least a portion of the cleansing matrix is disposed between the container's access port and the substrate's cleaning port or recess, wherein the substrate's cleaning port or recess is sized to accommodate a portion of the cleansing matrix and a valve portion of a needleless medical valve when the valve portion of the needleless medical valve is in sanitizing association with the cleansing matrix during a sanitizing operation.

11. An article according to claim 10, wherein the cleansing matrix comprises an absorbent material selected from the group consisting of a naturally occurring material and a synthetic material, wherein when the cleansing matrix is a naturally occurring material, the naturally occurring material is optionally a natural sponge, and wherein when the cleansing matrix is a synthetic material, the synthetic material is optionally selected from the group consisting of a fibrous composition, a foam, and a gel.

12. An article according to claim 10, wherein the sanitizing reagent is a liquid formulation, optionally an aqueous solution, optionally a solution comprising an alcohol and water, optionally isopropyl alcohol and water, optionally 70% isopropyl alcohol and water.

13. An article according to claim 10, wherein the sanitizing reagent comprises one or more sanitizing compounds selected from the group consisting of an alcohol, chlorhexidine, hydrogen peroxide, iodine, silver ions, and a combination of any two or more of the foregoing.

14. An article according to claim 10, wherein the laminated foil container comprises an upper portion and a lower portion, which upper and lower portions are sealed to each other about their peripheries.

15. An article according to claim 10, wherein an outer surface of the laminated foil container is labeled.

16. An article according to claim 10 that is sterile.

17. A package comprising a plurality of articles according to claim 10.

* * * * *